United States Patent [19]

Tyberg et al.

[11] Patent Number: 5,648,727
[45] Date of Patent: Jul. 15, 1997

[54] CAPACITIVE LEVEL SENSING PIPETTE PROBE

[75] Inventors: William T. Tyberg, Spring Valley, N.Y.; John W. Jones, Gwynedd, United Kingdom

[73] Assignee: DPC Cirrus Inc., Randolph, N.J.

[21] Appl. No.: 547,553

[22] Filed: Oct. 24, 1995

[51] Int. Cl.⁶ .................. B01L 3/02; G01F 23/24
[52] U.S. Cl. .............. 324/677; 324/667; 324/697; 324/671; 73/304 C; 422/106; 422/82.01
[58] Field of Search ............ 73/304 C; 422/100, 422/82.01, 82.02, 105, 106, 62; 324/697, 677, 678, 664, 671, 667

[56] References Cited

U.S. PATENT DOCUMENTS

| | | | |
|---|---|---|---|
| 4,025,846 | 5/1977 | Franz | 73/304 C |
| 4,429,272 | 1/1984 | Bungay | 324/678 |
| 4,970,468 | 11/1990 | Ishizawa | 324/662 |
| 5,032,794 | 7/1991 | Ridd | 324/697 |
| 5,045,286 | 9/1991 | Kitajima | 73/304 C |

*Primary Examiner*—Kenneth A. Wieder
*Assistant Examiner*—Jose M. Solis
*Attorney, Agent, or Firm*—Whitham, Curtis, Whitham & McGinn

[57] ABSTRACT

A capacitive fluid level sensing pipette probe adapted to be used in an automated random access immunoassay analyzer is provided. The pipette probe comprises an elongated shaft having a conductive tip. An integrated circuit chip containing capacitive sensing circuitry is positioned on the pipette probe itself, or in very close proximity. With this arrangement, the sensing circuitry moves with the pipette probe as it is raised and lowered into and out of a vessel containing a liquid. Thus, errors associated with capacitance caused by flexing connector cables is eliminated. Flex tape wiring may be used to carry data from the capacitive sensing circuitry on the pipette probe to the processing board of the automated immunoassay analyzer.

11 Claims, 5 Drawing Sheets

CAPACITIVE LEVEL SENSING PIPETTE PROBE

BACKGROUND OF THE INVENTION

1. Field of the Invention

The present invention generally relates to capacitive fluid level sensing and, more particularly, to a capacitive fluid level sensing pipette probe for use in an automated chemical analyzer, such as, for example, an automated immunoassay analyzer.

2. Description of the Prior Art

Many chemical analysis processes involve adding a reagent to a sample, allowing a chemical reaction to occur, and then analyzing the sample to determine its constitutes. An immunoassay is a well known type of chemical analysis method used to determine the amount of an analyte in a sample such as plasma or urine. It is based on the interaction of antibodies with antigens, and because of the degree of sensitivity for the analyte (either antigen or antibody), an immunoassay can be used to quantitatively determine very low concentrations of drugs, hormones, polypeptides, or other compounds found in a test sample.

Chemical analyses, such as immunoassays, were historically performed by hand by a trained laboratory technician. Recently, many companies have begun producing automated analyzers. Such systems are computerized and may utilize a conveyer chain or belt to convey sample vessels from station to station whereat specific analysis steps are carried out. The sample vessels may be bar coded to instruct the computer of its contents and the specific test which is to be performed on each sample. Based on this information, a precise volume of fluid is pipetted from a reagent container or a sample vessel to a test tube with a pipette probe.

Depending on the test to be performed, a multitude of reagents may be required. Some tests may even require a combination of several reagents. One way to prevent cross-contamination between samples, has been to use a separate pipette probe for each reagent. This is undesirable since it adds greatly to the mechanical complexity of the analyzer and requires an additional wash step for the pipette tip to reduce the level of contamination between the test samples and unspent reagent supply.

An automated immunoassay system must always generate results which are precise, accurate and independent of one another. These criteria are challenging to achieve since, typically laboratory workloads may demand that an automated system generate as many as 120 test results per hour. Although all instrument processes contribute to the instrument's ability to produce such results, perhaps none is more important than the pipetting process. As such, it is imperative that the pipette probe be able to transfer liquids precisely and accurately, with virtually no sample-to-sample carryover. It is also important to be able to sense when a pipette probe has just contacted a fluid surface. For container tubes containing only a small amount of liquid it is imperative that the pipette probe stop prior to the tip of the probe crashing into the bottom of the tube.

One way to minimize cross contamination and prevent bottom crashes is to accurately detect the fluid level in a tube containing a sample or a reagent. U.S. Pat. No. 4,897,244 to Wallace et al. is directed to a level sensing arrangement for sensing the descent of a probe into a fluid. A container containing a fluid sample rests on a flat, grounded surface. A probe is connected to an AC signal source. A cable connects the probe to a remote impedance sensing circuit. When the probe is lowered and contacts the fluid sample, the remote impedance sensing circuit senses an increase in capacitance. A control circuit uses the impedance information to operate a mechanical drive. The impedance measurements are used to determine the depth of the probe in the container.

As discussed above, a capacitive level sensing circuit must be able to accurately detect when the tip of the probe has just touched the fluid surface. Unfortunately, the above described circuit suffers from some drawbacks. Referring to FIG. 1, while the sensing element is the probe 2 itself, the sensing circuitry 4 is located elsewhere and is connected to the probe by a coaxial cable 6. The nature of the co-axial cable allows the cable to bend and flex. This is understandable since the sensing circuitry 4 is stationary and the probe 2 is mobile, that is, its function is to repeatedly raise and lower into a vessel 8 containing fluid. The coaxial cable on available probes is upwards of six inches long and itself has a capacitance upwards of 20 pf. Additionally, the flexing of the cable can cause a change in capacitance of up to 1 pf, unrelated to the position of the probe relative to the fluid.

Since the quantifies of fluid aspirated by the probe is extremely small, often in the order of microliters, the capacitance change when the probe tip contacts the fluid may often be less than 1 pf. Hence, errors will occur since the control circuitry will mistake the capacitance change due to the flexing of the cable for the expected change due to the probe tip contacting the fluid.

SUMMARY OF THE INVENTION

It is therefore an object of the present invention to provide a pipette probe having highly precise capacitive level sensing abilities;

It is yet another object of the present invention to provide a pipette probe tip which has sensing circuitry mounted directly on the probe thereby eliminating the need for a cable.

It is yet another object of the present invention to provide a pipette probe with minimal carryover contamination from one test vessel or reagent vessel to another.

The invention is directed to a capacitive sensing pipette probe adapted to be used in an automated random access immunoassay analyzer. The pipette probe of the present invention comprises an elongated shaft having a conductive tip. An integrated circuit chip containing capacitive sensing circuitry is positioned on the pipette probe itself, or in very close proximity. With this arrangement, the capacitive sensing circuitry moves with the pipette probe as it is raised and lowered. Thus, there is no cable to flex and cause errors. Flex tape wiring may be used to carry data from the capacitive sensing circuitry on the pipette probe to the processing board of the automated immunoassay analyzer.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
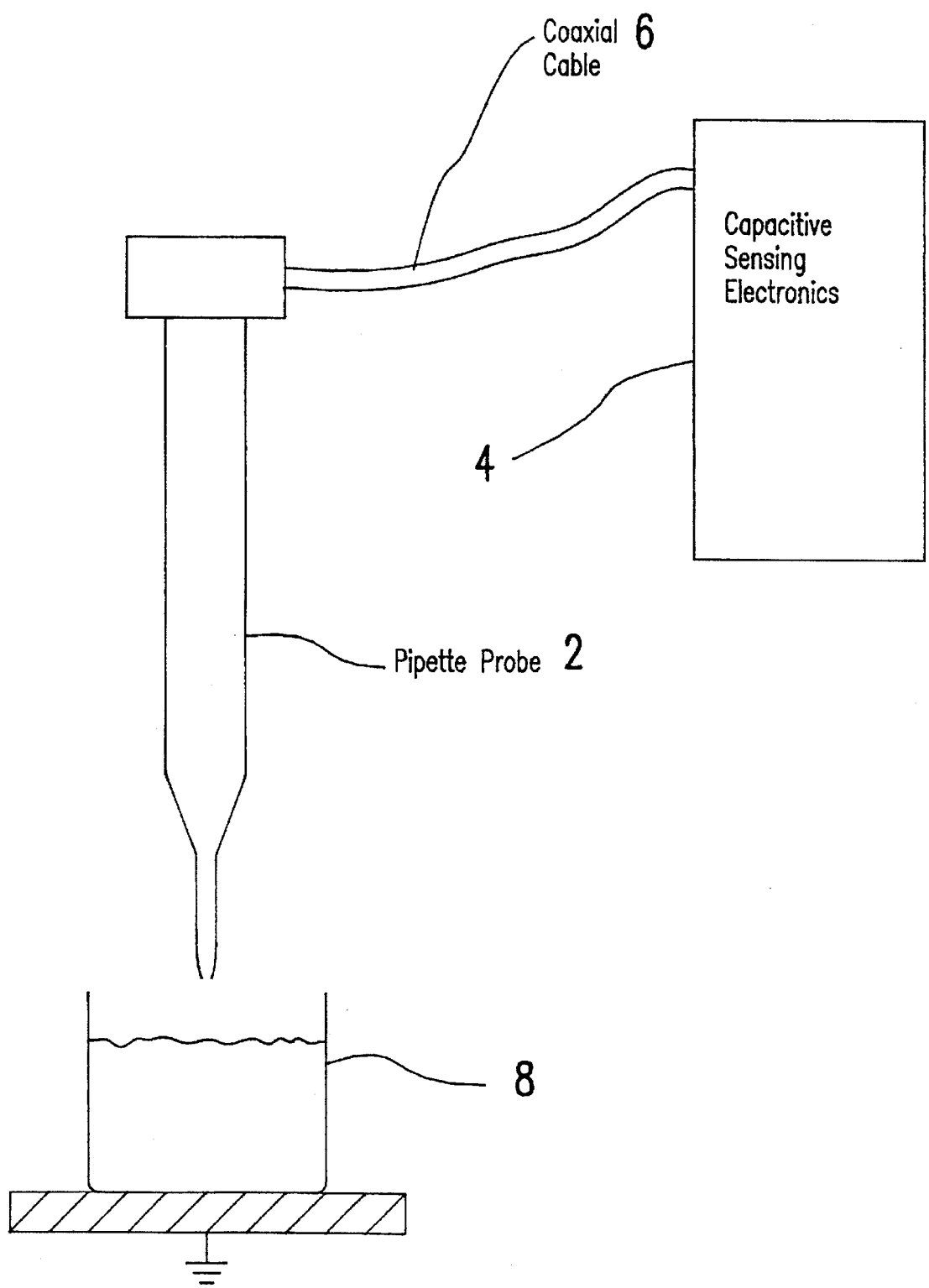
FIG. 1 is a block diagram of a conventional capacitive level sensing arrangement.
Figure 2:
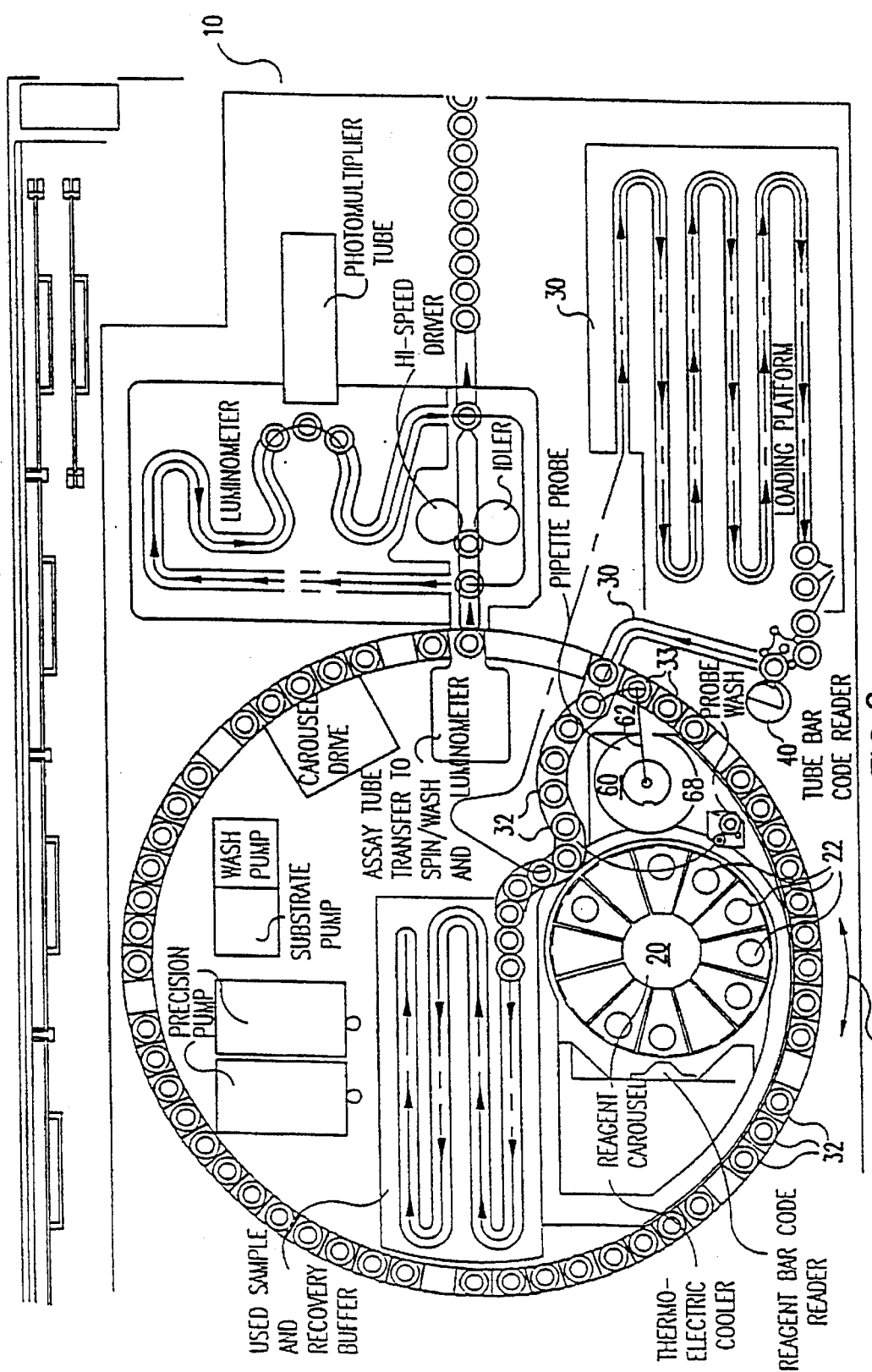
FIG. 2 is schematic showing an automated random access immunoassay analyzer.

Referring now to the drawings, and more particularly to FIG. 2, there is shown a schematic of an automated random access immunoassay analyzer of the type which will benefit from the probe of the present invention. The analyzer accepts small sample vessels of patient sera, along with assay-specific test units and reagents appropriate to the completion of a wide variety of immunoassays. Through appropriate manipulation of these articles, the instrument produces clinically significant results useful in the quantitation of many heath related parameters.

The automated analyzer, generally referred to by reference numeral 10, incorporates two distinct areas into which the user loads items necessary to instrument function. These include the reagent carousel 20 and the load chain 30. The reagent carousel 20 can accommodate up to twelve different prepackaged liquid reagent units 22, each suitable for the performance of a different immunoassay. The load chain 30 is an endless conveyor which accepts a large number of tubes 32 for testing. The tubes 32 may either be used to carry sample sera or for carrying immunoassays. The tubes 32 are bar-coded and automatically recognized by the analyzer 10 by bar code reader 40. As the chain 30 advances, serum from a sample tube 32, along with the appropriate liquid reagent (s) from the reagent carousel 20, is pipetted into the immunoassay tubes 33 at the pipetting station 60. The pipetting station 60 includes a pipette probe projecting downward (into the page) from an arm 62. The arm 62 travels in a circular path and can access a plurality of tubes 32 as well as reagents 22. Between each pipetting cycle, the pipette probe is washed at wash station 68 to reduce carryover contamination between the reagents 22 and tubes 32.

The pipette tip performance is perhaps the single most important factor contributing to accurate immunoassay test results. The pipette tip performance requirements for an automated immunoassay analyzer, such as that shown in FIG. 2, dictate that pipetting precision must be less than 1% CV, the accuracy greater than 96% sample recovery, the sample to sample carryover must be less than 10 ppm, and it must be fast enough to do all necessary steps in 30 seconds or less. As a practical matter, it is readily apparent that accurate capacitive level sensing in imperative if these demands are to be met.

Figure 3:
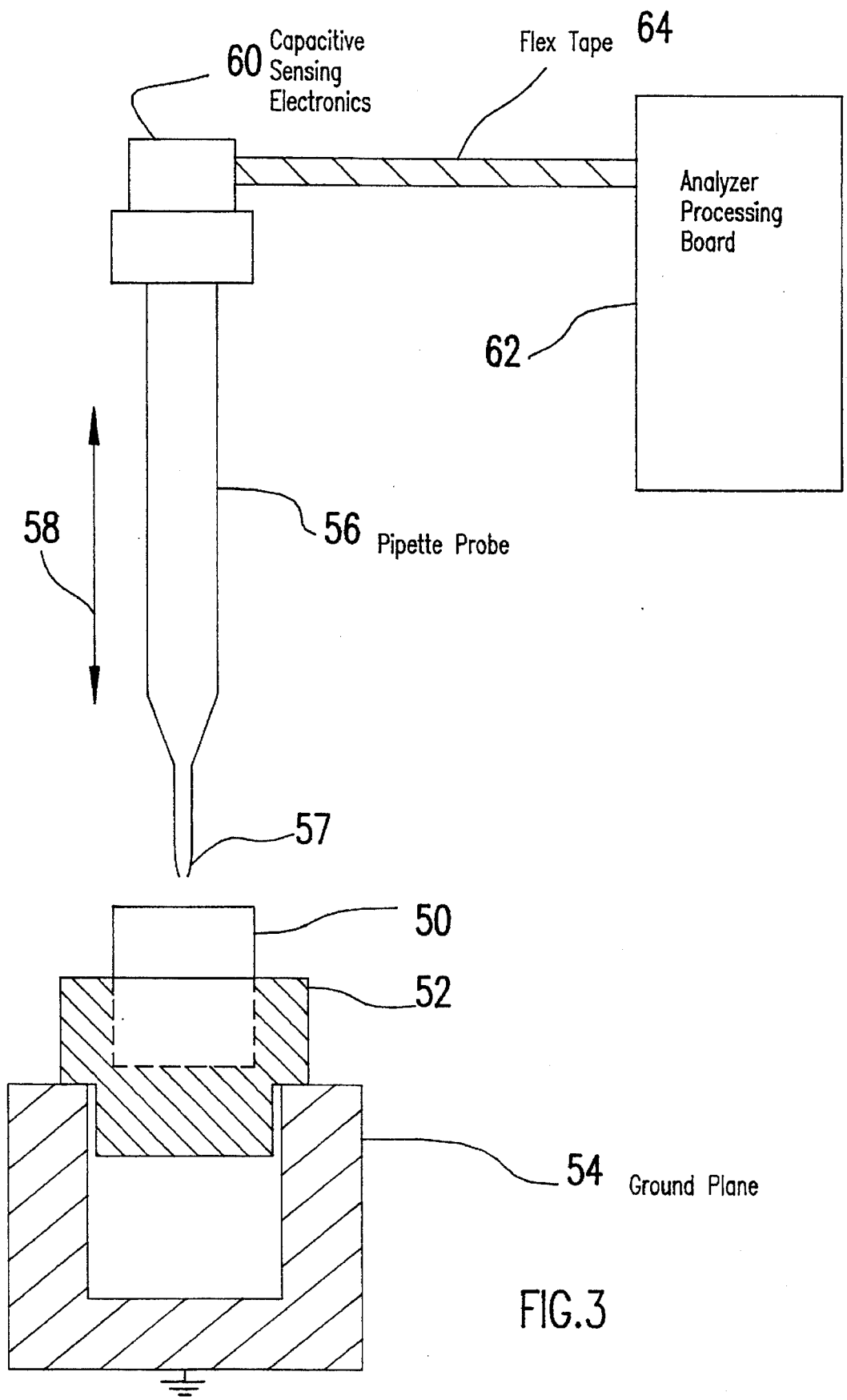
FIG. 3 is a block diagram showing a conventional capacitive sensing arrangement having remotely located sensing circuitry connected to the probe with a coaxial cable.

FIG. 3 shows a block diagram of the capacitive level sensing circuit according to the present invention. A tube 50 containing a fluid sits in a plastic holder 52 which in turn rests in a U-shaped ground plane. A pipette probe 56, comprising a hollow, elongated tube, is designed to move up and down in the direction of the arrow 58. The pipette probe is preferably comprised of stainless steel of some other electrically conductive material. Capacitive level sensing circuitry 65 is integrated onto a chip and located directly on the probe 56. Hence, there are no cables or wires to flex and bend as the probe 56 is raised and lowered. In the drawing, the sensing circuitry is shown on top of the probe 56; however, it is understood that the sensing circuitry may be located elsewhere on the probe 56 or in very close proximity to the probe. The capacitive sensing circuit is connected to an analyzer board 2 of the with flex tape 64 or some other flexible conductor.

In operation, the probe 56 raises and lowers into the tube 50 along path 58, the capacitive level sensing circuitry 60 moves with the probe 56. Due to the dielectric constant of the fluid in the tube 50, the capacitance between the probe and the ground plane 54 will instantly increase when the probe tip contacts the fluid. The level sensing circuitry 60 outputs a level sensing signal over the flex tape 64. Even though the flex tape 64 moves as the probe 56 is raised and lowered, the capacitance level sensing has already been calculated by this point in the circuit. Hence, any generated capacitance or other unwanted noise that may be caused by the movement in the flex tape 64 will have no bearing on the determination of the probe 56 level.

Figure 4:
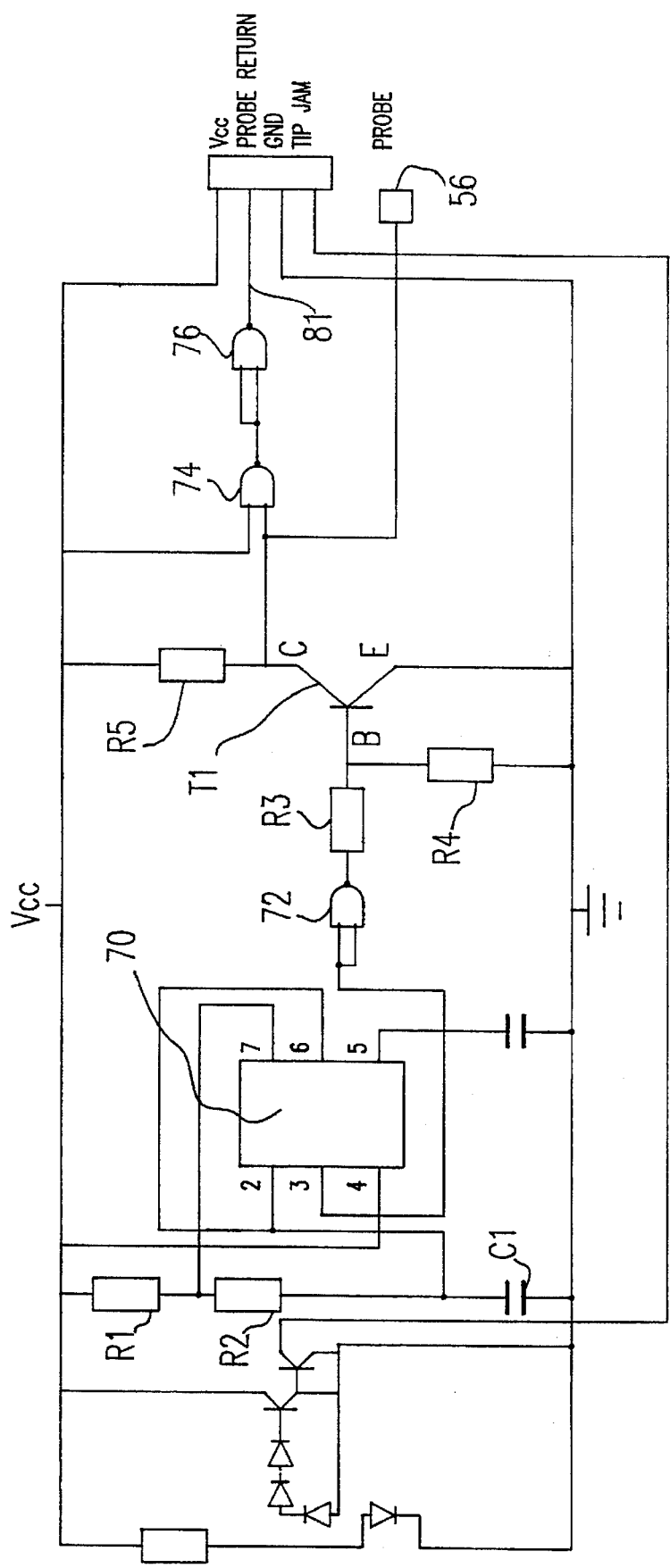
FIG. 4 is a circuit schematic of the capacitive level sensing circuitry located on the probe.

FIG. 4 shows a circuit schematic for the capacitive level sensing circuit 60. An oscillator 70 is connected to resistors R1, R2, and capacitor C1 which causes the oscillator to oscillate at a frequency of 200–300 KHz. The base electrode of a transistor T1 is connected to an oscillating inverter buffer NAND gate 72, through resistor R3 and across resistor R4. The oscillator 70 turns the transistor T1 on and off at a frequency of 200–300 KHz. Both inputs of the NAND gate 72 are tied together to provide a sharp square pulse to the transistor T1. NAND gate 74 has its first input tied to Vcc and its second input connected to the collector of the transistor T1 and pulled-up to Vcc via R5. This reduces stray capacitance. When the transistor T1 is on, current flows from the collector to the emitter of T1 thus connecting the second input of NAND gate 74 to ground and holding the NAND gate 74 output in a high state. The conductive probe 56 is electrically connected to the collector of the transistor T1. When the oscillating inverter buffer 70 turns the transistor T1 to an off state, it stops conducting and effectively connects the second input of the NAND gate 74 to Vcc through pull-up resistor R5. Hence, the switching time for the NAND gate 74 is a function of the RC time constant determined by the pull-up resistor R5 and the capacitance of the probe 56. NAND gate 76 has both of its dual inputs tied to the output of NAND gate 74 and serves to sharpen the output of the NAND gate 74. The output of NAND gate 76 is shown labeled as PROBE RETURN and is a square wave having a width which is a function of the capacitance on the probe 56.

Figure 5:
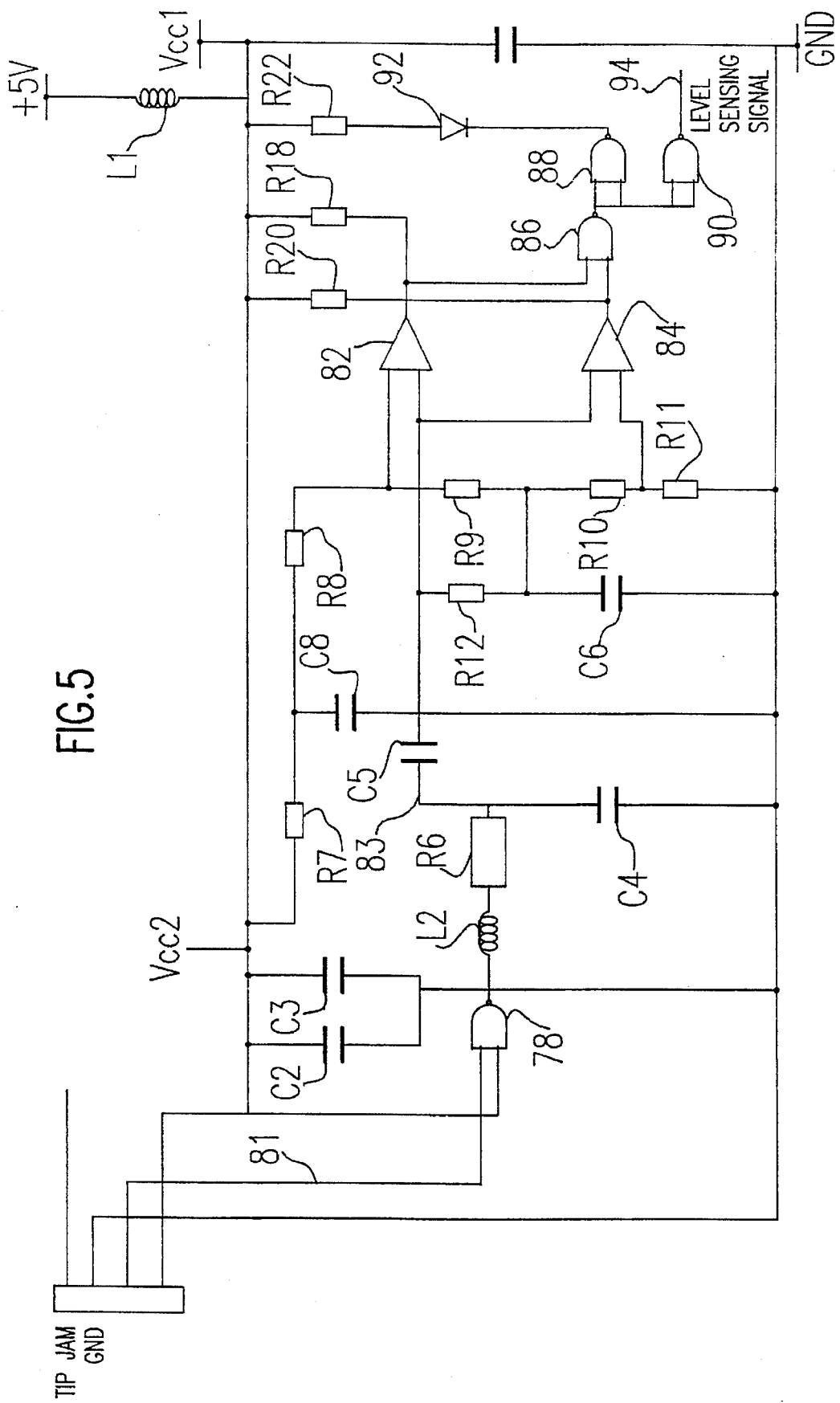
FIG. 5 is a circuit schematic of the capacitive level sensing signal conditioning circuit.

FIG. 5 is a capacitive level sensing signal conditioning circuit 80 receiving as an input the PROBE RETURN output of NAND gate 76. The conditioning circuit 80 may be located off the probe 56 and connected to the sensing circuit 60 of FIG. 4 via a connector, such as, for example, the flex tape connector 64 shown in FIG. 3. The conditioning circuit 80 preferably comprises filtering elements comprising capacitors C2 and C3 and inductor L1 to filter voltage Vcc.

The PROBE RETURN signal 81 is connected to a first input of a NAND gate 78 and the second input is tied to Vcc. The NAND gate 78, like NAND gate 76, serves to square-up or sharpen the PROBE RETURN signal 81 which is then passed through a low-pass filter comprising an inductor L2, resistor R6, capacitor C4, and differentiator capacitor C5. The low pass filter converts the pulse width of the PROBE RETURN signal 81 into a direct current (dc) voltage signal 83, where the wider the pulse width, the high the dc voltage signal 83 will be. A voltage divider circuit comprising resistors R7, R8, R9, R10, and R11 is provided to set up reference voltages for comparators 82 and 84. A capacitor C8 to eliminate noise may be inserted between R7 and R8. The outputs of comparators 82 and 84 are connected to pull-up resistors R18 and R20, respectively. Bias for the comparators 82 and 84 is developed by the voltage between R9 and R10. Capacitor C6 and resistor R12 serve as a filter.

The nominal biased dc voltage signal is input into the inverting input of the first comparator 82 and into the non-inverting input of the second comparator 84. The non-inverting input of the first comparator 82 is connected to the voltage divider between resistors R8 and R9 and the inverting input of the second comparator 84 is connected to the voltage divider between resistors R10 and R11. Hence, the first comparator 82 is biased slightly above the nominal level of the dc voltage signal while, the second comparator 84 is biased slightly below the nominal level of the de voltage signal. The output terminals of each of the comparators 82 and 84 is connected to the input terminals of a dual input NAND gate 86.

In operation, when the probe 56 is lowered and just touches the surface of a fluid, the capacitance on the probe will instantly increase causing the PROBE RETURN signal to output a wide square pulse. This increase causes the de voltage signal 83 to raise above the nominal bias level and cause the first comparator 82 to change its output signal. This activates NAND gate 86, the output of which is tied to the inputs of smoothing NAND gates 88 and 90. Hence, when the first comparator activates as the probe touches the fluid, an LED 92, biased with resistor R22, flashes. In addition, NAND gate 90 outputs a pulse level sensing signal 94. When the probe is raised and just pulls out of the fluid, the capacitance of the probe will instantly decrease and be detected by the second comparator 84. Again, this will cause the LED 92 to flash and will cause NAND gate 90 to pulse a level sensing signal 94. The level sensing signal may be feed to control circuitry (not shown) which controls the raising and lowering of the probe 56.

The table below shows test data for various capacitative level sensing circuits and for the probe having a chip containing the capacitive sensing circuitry positioned directly on the pipette probe itself according to the present invention:

| Circuit Type | Minimum Volume Detected |
| --- | --- |
| 1. EURO-DPC #014 | 45 µL |
| 2. EURO-DPC #011 | 40 µL |
| 3. EURO-DPC #010 | 35 µL |
| 4. EURO-DPC #009 | 45 µL |
| 5. B-5 | 60 µL |
| 6. D-353 | 50 µL |
| Present invention EURO-DPC #008 with chip on probe | 25 µL |

A computer program was repeatedly run with various levels of PBS 0.01M placed into sample cups. Fluid levels began at 100 µL and continued down in 5 µL steps until 10 µL of fluid remained in the sample cup. A syringe was attached to the probe tubing to blow out any fluid that wicked up inside of the probe. Successful level detection was determined if the probe did not bottom out in the sample cup during ten complete up and down movements. These movements were carefully watched for errors and false level detection signals. During tests with less than 30 µL of fluid, the probe may have removed fluid from the sample cup. If errors happened repeatedly, a new sample cup with the correct volume of fluid was tested again. From these tests it should be noted that conventional level sense circuitry connected to the probe via a cable was able to detect between 35 µL to 60 µL of fluid in the sample cup. The probe of the present invention, having the sensing circuitry mounted on the probe itself, was able to accurately detect as little as 25 µL of fluid in the sample cup which is an improvement over conventional capacitive level sensing circuits.

While the invention has been described in terms of a single preferred embodiment, those skilled in the art will recognize that the invention can be practiced with modification within the spirit and scope of the appended claims.

I claim:

1. A capacitive fluid level sensing probe for raising and lowering into a vessel containing a fluid in an automated immunoassay analyzer, said probe comprising:
   a hollow shaft;
   a tip for drawing a fluid sample for an immunoassay into said hollow shaft, said tip having an electrically conductive portion; and
   fluid level sensing circuitry positioned to raise and lower with said probe, said fluid level sensing circuitry being in electrical contact with said tip for sensing a capacitive change when said tip contacts the fluid.

2. A capacitive fluid level sensing probe as recited in claim 1 wherein said fluid level sensing circuitry is in the form of an integrated circuit chip positioned on said probe.

3. A capacitive fluid level sensing probe as recited in claim 1 wherein said fluid level sensing circuitry outputs a fluid level sensing signal to remote circuitry via a flex-tape connector.

4. A capacitive fluid level sensing probe as recited in claim 1, further comprising;
   oscillating means for generating an oscillating pulse;
   switch means connected to said oscillating means and being turned to an on state and an off state by said oscillating pulse;
   a resistor electrically connected to said tip of said probe when said switch is in said off state; said fluid level being sensed as a function of an RC time constant of said resistor and a capacitance on said tip when said tip contacts fluid.

5. A capacitive fluid level sensing probe as recited in claim 4, further comprising a conditioning circuit;
   means for converting a rise time for said RC time constant into a square wave having a width which is a function said capacitance on said probe;
   means for converting said square wave into a direct current voltage level;
   comparison means for comparing said direct current voltage level to a reference level and outputting a level sensing signal when said direct current voltage level differs from said reference level.

6. A capacitive fluid level sensing probe as recited in claim 5 wherein said comparison means comprises a first comparator and a second comparator.

7. A capacitive fluid level sensing probe as recited in claim 6, further comprising:
   a biasing means for biasing said direct current voltage level to a nominal voltage level signal, said nominal voltage level signal being input into said first comparator and said second comparator;
   a voltage divider for providing a high reference voltage to said first comparator and a low reference voltage to said second comparator, wherein said first comparator causes a level sensing signal output when said tip contacts a fluid and said second comparator causes a level signal output when said tip is removed from fluid.

8. A pipette probe for an automated immunoassay analyzer able to precisely detect when a probe tip enters and leaves a fluid; comprising:
   an elongated shaft being tapered at a tip end;
   an electrical contact at said tip end; and an integrated circuit chip, integral with said probe, for sensing a capacitance on said electrical contact, said integrated circuit chip measuring an increase in capacitance when said tip end contacts a fluid and measuring a decrease in capacitance when said tip is removed from fluid.

9. A pipette probe for an automated fluid analyzer as recited in claim 8 wherein said integrated circuit chip outputs a probe signal as a square wave having a width proportional to a capacitance on said tip.

10. A method for detecting capacitance on a pipette probe tip, comprising the steps of:

tying a first input of a first logic gate to a logic high voltage;

connecting a second input of said first logic gate to a switch and to a pipette probe tip;

oscillating said switch to alternately connect said second input of said first logic gate to electrical ground and to said logic high voltage through an impedance circuit, said impedance circuit having an RC time constant proportional to a capacitance on said pipette probe tip, said first logic gate outputting a square wave having a width which is function of said RC time constant.

11. A method for detecting capacitance on pipette probe tip as recited in claim 10 further comprising the step of:

connecting all inputs of a second logic gate to an output of said first logic gate to produce a square wave having a width which is function of said RC time constant and having sharpened corners.

* * * * *